United States Patent [19]
Fox

[11] Patent Number: 5,990,382
[45] Date of Patent: Nov. 23, 1999

[54] METHOD AND IMPLANT FOR SURGICAL MANIPULATION OF BONE

[75] Inventor: William Casey Fox, Pipe Creek, Tex.

[73] Assignee: BioMedical Enterprises, Inc., San Antonio, Tex.

[21] Appl. No.: 08/413,603

[22] Filed: Mar. 30, 1995

Related U.S. Application Data

[63] Continuation-in-part of application No. 08/016,908, Feb. 12, 1993, Pat. No. 5,405,388, application No. 08/357,072, Dec. 15, 1994, and application No. 08/383,829, Feb. 6, 1995, which is a continuation-in-part of application No. 08/016,908, and application No. 08/357,072, which is a continuation of application No. 08/194,812, Feb. 11, 1994, abandoned, which is a continuation of application No. 08/062,735, May 10, 1993, abandoned, which is a continuation of application No. 07/924,420, Jul. 30, 1992, abandoned, which is a continuation of application No. 07/575,001, Aug. 29, 1990, abandoned.

[51] Int. Cl.$^6$ .................................................. A61F 2/28
[52] U.S. Cl. ............................................................ 623/16
[58] Field of Search ................................. 623/16, 18, 20, 623/11; 606/164, 167, 130; 604/256, 265, 167; 128/898

[56] References Cited

U.S. PATENT DOCUMENTS

| | | |
|---|---|---|
| 3,896,504 | 7/1975 | Fischer . |
| 4,438,773 | 3/1984 | Letterio . |
| 4,681,103 | 7/1987 | Boner et al. . |
| 4,772,261 | 9/1988 | Von Holf ................................. 604/51 |
| 4,805,634 | 2/1989 | Ullrich et al. . |
| 4,880,006 | 11/1989 | Alberktsson ............................ 128/630 |
| 4,936,851 | 6/1990 | Fox ........................................... 623/16 |
| 5,385,553 | 1/1995 | Hart et al. ............................... 604/167 |
| 5,405,388 | 4/1995 | Fox ........................................... 623/16 |
| 5,569,205 | 10/1996 | Hart et al. ............................... 604/167 |

FOREIGN PATENT DOCUMENTS

| | | |
|---|---|---|
| 17592 | 1/1913 | United Kingdom . |
| 1548964 | 7/1979 | United Kingdom . |

OTHER PUBLICATIONS

International Search Report for related foreign application PCT/US96/04350, date of mailing Aug. 19, 1996.

Aufdemorte, T.B., Fox, W.C., Boyce, R.F., Triplett, R.G., Poser, J., Moore, G., and Holt, G.R., "A novel orthopedic implant to repeatedly sample cancellous bone for histomorphometric analysis," 5th International Congress of Bone Morphometry, Niigata, Japan, Jul. 1988.

Aufdemorte, T.B., Fox, W.C., Holt, G. H., Triplett, R.G., McGuff, H. S., Nguyen T., Ammann, A.J., and Beck, S.L., "An Intraosseous Device for the Study of Osteotropic Factor Effects and Bone Healing: A Trial with Transforming Growth Factor–$\beta_1$ (TGF–$\beta_1$ )," Journal of Bone and Joint Surgery, 74–A,8:1153–61, Sep. 1992.

(List continued on next page.)

*Primary Examiner*—David J. Isabella
*Attorney, Agent, or Firm*—Akin, Gump, Strauss, Hauer & Feld, L.L.P

[57] ABSTRACT

A method and implant for surgical manipulation of bone consist of methods and devices to sample bone (21 and 23) and marrow, (22) and perform skeletal surgery from the inside of the bone. The method uses a hollow cylinder (13 or 15) inserted permanently or temporarily into a drill hole in a bone which acts as a port. To this port, adapters (27) can be used to guide fiber optics (31); surgical devices, such as rotating cutters (32); and aspiration or infusion catheters (33). The ability of the insert (13 or 15) to seal in bone allows the collection of tissue under sterile conditions for transplantation to other sites in the patient. The aspiration and collection capability of this method and device allows the aspirate to be processed aseptically, to be concentrated to its vital components, and combined with donor or synthetic bone material for the treatment of bone at a distant skeletal site. This distant site might be accessed with the insert (13 and 15) and infusion catheter (33) or with conventional surgical technique.

24 Claims, 5 Drawing Sheets

OTHER PUBLICATIONS

Fox, W. C., "Osseous Implants for Experimental Studies of Bone, Marrow, and Materials Biocompatibility," Dissertation, The University of Texas at Austin, pp. 19–37, May 1991.

Fox, W. C. and Miller, M. A., "An Osseous Implant for Studies of Biomaterials Using an In–vivo Electrochemical Transducer," Journal of Biomedical Materials Research, 27:763–773, Jun. 1993.

Fox, W. C. and Aufdemorte, T. B., "Experience with Osseous Implants for Bone and Biomaterials Research," Journal of Long–Term Effects of Medical Implants, 3,1:1–27, Apr. 1993.

Alberktsson and Linder, "A Method for Short–and Long–term In vivo Study of the Bone–Implant Interface", Jn Clin. Ortho. Rel. Res 159:269–273 Sep. 1981.

Alberktson, Branemark, Hansson and Lindstrom, "Osseointegrated Titanium Implants: requirements for ensuring a long–lasting, direct bone–to–implant anchorage in man," Acto orthop. scand. 52, 155–170, 1981.

Drinker C.K., Drinker K.R., Lund C.C., The circulation in the mammalian bone marrow. Am j Physiol 1922; 62:1–92.

Tocantis, L.M., O'Neill J.F., Price A.H., Infusion of blood and other fluids via the bone marrow in traumatic shock and other forms of peripheral circulatory failure, Ann Surg 1941;114:1085–1092.

Meola, F., Bone marrow infusions as a routine procedure in children, J Pediatr 1949;25:13–16.

Heinild S., Sondergaard T., Tudvad F., Bone marrow infusions in childhood: Experiences from a thousand infusions, J Pediatr 1947;30:400–412.

Papper E.M., Bone marrow route for injecting fluids, drugs into general circulation, Anesthesiology 1942;3:307–313.

Rosetti V.A., Thompson B.M., et. al., Intraosseous infusion: An alternative route of pediatric intravascular access, A Emer Med 1985; 14.9;103–105.

Valdes M.M., Intraosseous fluid administration in emergencies, Lancet 1977;2:1235–1236.

Shoor P.M., Berryhill R.E., Benumof J.L., Intraosseous infusion: Pressure–flow relationship and pharmacokinetics, J Trauma 1979;19:772–774.

U.S. application No. 08/357,072, Fox, filed Dec. 15, 1994.

METHOD AND IMPLANT FOR SURGICAL MANIPULATION OF BONE

FIELD OF THE INVENTION

The invention described relates broadly to bone implants and surgical devices, and generally to the field of medical devices that support the surgical manipulation of bone, marrow and cartilage. This application is a continuation-in-part application of U.S. Ser. No. 08/383,829 filed Feb. 6, 1995, of U.S. Ser. No. 08/357,072 filed Dec. 15, 1994, and of then U.S. Ser. No. 08/016,908 filed Feb. 12, 1993, since issued as U.S. Pat. No. 5,405,388, Apr. 11, 1995. U.S. Ser. No. 08/383,829 is a continuation-in part application of U.S. Ser. No. 08/357,072, and of U.S. Ser. No. 08/016,908. U.S. Ser. No. 08/357,072 is a continuation of U.S. Ser. No. 08/194,812 filed Feb. 11, 1994, now abandoned, which was a continuation of U.S. Ser. No. 08/062,735, filed May 10, 1993, now abandoned, which was a continuation of U.S. Ser. No. 07/924,420 filed Jul. 30, 1992, now abandoned, which was a continuation of U.S. Ser. No. 07/575,001 filed Aug. 29, 1990, now abandoned.

The patent and each pending patent application is incorporated by reference herein.

BACKGROUND

U.S. Pat. No. 4,936,851 issued Jun. 26, 1990 to Fox et al., describes a device that allows cancellous bone and marrow as well as organs surrounded by hardened cortical bone to be accessed repeatedly from the same site with minimal surgical trauma and morbidity. The purpose of gaining repeated access was to provide a means for obtaining a significant sample of cancellous tissue for histologic and morphometric analysis.

U.S. Ser. No. 08/357,072, provides a cancellous access port that can be used for repeated biopsies of osseous tissue.

Through repeated use of the prior art devices, failures of the mechanism, difficulty in surgical placement and the inability to acquire a biopsy have been encountered. To overcome these deficiencies; the Bone Biopsy Implant (BBI) (Ser. No. 08/016,908 filed Feb. 12, 1993), since issued as U.S. Pat. No. 5,405,388, Apr. 11, 1995 was conceived. The bone biopsy implant forms a port allowing endoscopic access to the medullary compartment.

In the prior art, bone implants have been used to solve health care problems of orthopedic and maxillofacial reconstruction, prosthesis and denture fixation, and fracture stabilization. Additionally, bone implants have been developed to advance the knowledge of bone healing and remodeling as well as the interaction of bone and implant material or devices.

Prior art includes an optical titanium chamber disclosed by Albrektsson in 1979, a bone ingrowth chamber (Albrektsson et al., U.S. Pat. No. 4,880,006, Nov. 14, 1989), and a bone harvest chamber (hereinafter sometimes called the "BHC") (Kalebo in 1987) all of which were developed at the University of Goteborg, Sweden. Prior art devices provide a means for obtaining permanent atraumatic access to otherwise inaccessible biological tissues which are protected or covered by hardened bone structures. However, their capability to obtain a biopsy of cortical bone or cancellous tissue following complete healing and mineralization of this tissue is severely compromised by their design.

The osseous infusion capability of the implant system builds on the use of long bones for acute access to the cardiovascular system which dates back to 1922 when Drinker first suggested the sternum as an infusion route. In the early 1940's, Tocantins laid the basis for widespread application of tibial and sternal routes for the administration of fluids to the cardiovascular system.

Building on Tocantins work Meloa, Heinild and Papper demonstrated clinical application of this route for access to the vascular system in children and adults. Heinild reported the use of a needle to infuse 495 patients in which 982 procedures were performed to treat seventeen indications and one general category of disease. In this three year study, only eighteen unsuccessful attempts were reported. Though deaths of patients in the treatment groups were reported, none were specifically attributed to the infusion procedure. In this group of patients, the majority received multiple infusions with one individual receiving as many as ten. Historically, a wide range of fluids have been infused (blood, serum, saline, etc.). Irritation and pain were reported with the infusion of hypertonic solutions. This observation indicates there might be a considerable risk of osteomyelitis when hypertonic solutions are infused via this route.

Complications with these procedures were reported. Heinild reported that clinically, 8.2% of the initial attempts to enter the medullary cavity with a needle failed. Cases in which multiple attempts were made to enter the medullary cavity, only 1.8% were a complete failure. Some cases reported a large hematoma on the posterior aspect of the leg suggesting that the needle had been pushed through the bone. Swelling and oozing around the entry site were noted suggesting that retrograde flow around the needle was occurring. Technical difficulties such as bending and sticking of the needle were also reported. In a 1985 review of the procedure, Rosetti summarized reports by 30 authors between 1942 and 1977 of 4359 attempted infusions. Of these 4359 attempts, 89 were complete failures. Additionally, 27 incidences of osteomyelitis and 10 other complications occurred.

Presently, cannulation is used as a standard method for emergency resuscitation for infants. Valdes reported its use in 15 adults with a mean age of 50.46 years. Shoor investigated the pressure-flow relationship and pharmacokinetics of the procedure. Infusion rates from 102 to 2,500 ml/hour were reported with gravity feed and pressures up to 300 mmHg in the tibia and sternum. Rosetti reported data on infusion rate, fluids administered, uses, complications and suggested intraosseous infusion as an alternative route for pediatric intravascular access. The American Heart Association supports Rosetti's recommendations and suggests the procedure as a recommended alternative for circulatory support for pediatric care.

In the prior patent art an implant invented by Von Hoff et al. entitled "Intramedullary Catheter" (U.S. Pat. No. 4,772,261) is described. This patent describes a method and bone implant device to facilitate osseous infusion. The intramedullary catheter (IC) patent claims a method that uses an elongated, tubular conduit, and a head attached to one end of the conduit. Dependent claims describe a sealing mechanism disposed in the cavity to overly the conduit. The combination of the elongated, tubular conduit, head, cavity and sealing mechanism were well known in the technical literature but were novel due to their combination as a permanent implantable device.

The title intramedullary catheter and claims describe a device that resides in bone marrow and relies on a tubular conduit connected to the outside of the bone to facilitate infusion. Blockage of this conduit would and in reports has caused the device to fail during human and animal use. The internal volume of the conduit and cavity form dead space within the human body. The body naturally tries to fill this space which results in blockage of the device and its failure to facilitate osseous infusion. The dead space formed by the conduit and cavity provide an region within the implant that is prone to microbial colonization and intractable infection.

The principal deficiencies of the IC are conduit and cavity blockage, microbial colonization, exfoliation of the implant, difficulty in surgical placement and the inability to replace the sealing means or clear the device without explantation. Explantation of the device generally damages the surrounding bone leaving the site unsuitable for future use.

The subject invention of the present patent application is related to the bone biopsy implant. The present disclosure details the use of devices for endoscopic and other access and includes teaching for minimally invasive surgical manipulation of bone. The subject invention expands on the use of the bone biopsy implant for endoscopic access to the medullary compartment by describing a method of performing bone surgery, viewing bone and marrow tissue, delivering materials to bone and fluids into the cardiovascular system and aspirating fluids from a patient through an implant that forms a port through a surgically created defect in bone tissue.

SUMMARY OF THE INVENTION—OBJECTS AND ADVANTAGES

The subject invention relates to a hard tissue implant device that acts as a port into bone for the manipulation of marrow, bone or cartilage. The subject invention, an implant for surgical manipulation of bone, builds on cancellous access port and bone biopsy implant technology (U.S. Ser. No. 08/357,072 and U.S. Pat. No. 5,405,388, previously incorporated herein by reference). The proper method for use of an osseous infusion implant is for it to provide a port into bone. It should not reach into the bone for it may damage the local medullary tissue and cardiovascular system. This port should just maintain an opening into the medullary compartment by restricting cortical bone from healing and closing this access port. The port should provide a means for inserting various assemblies that support several modalities of treatment. The treatments require a means for biopsy of local bone, introduction of surgical instruments such as fiber optics for viewing or surgery, flexible shaft cutters, suction instruments and infusion catheters.

To facilitate percutaneous osseous infusion, the port allows the insertion of an assembly into its bore that has a means to secure it to the port and a penetrable non-osseous-integrating plug that fills the bore of the port on one end reaching from the medullary compartment of bone to the overlying soft-tissue space. This implant does not form an elongated conduit that can plug but resembles a plug that has a length less than its diameter. This length is approximately equal to the thickness of the bone cortex.

The placement of a non-osseous-integrating plug that contacts both medullary tissue and the overlying soft-tissue eliminates the conduit, cavity and possibility of implant blockage and reduces the chance of microbial colonization. Having the non-osseous-integrating plug contact or be in close proximity to the bone blood supply eliminates the potential for bone to heal in or under the device thus separating it from the bone medullary vasculature.

Experimental studies have demonstrated that bone will not heal in direct contact with synthetic polymers. Silicone elastomers, polyethylene and teflon are examples of materials that are non-osseous-integrating and could be penetrated with a needle.

Further advantages consist of the ability to remove and replace the penetrable plug assembly without removing the port and damaging the surrounding cortical bone. This allows the replacement of the plug if it has been damaged by numerous needle insertions or if it has become infected. Additionally, if blockage of the bone occurs proximal or distal to the implant, the assembly can be removed and flexshaft driven cutters can be introduced to open the blockage and restore access to the cardiovascular system. Further advantages can be achieved by combining the biopsy assembly of the bone biopsy implant (U.S. Pat. No. 5,405,388, previously incorporated by reference herein) with the penetrable plug so that both osseous infusion and sampling can be accomplished with the same device.

The implants of the present invention that act as a port into osseous structures for the introduction of surgical instruments for viewing, cutting, cauterizing, aspirating, biopsying and infusing substances are novel.

The objects and advantages are: a collar (FIGS. 1 and 5: 15 and FIGS. 3 and 6: 13) having a bore (12) that forms a port into bone that can be used in a threaded or smooth drilled osseous defect, a contoured cap (FIGS. 2 and 5: 20) or adapter insert (27) to minimize overlying soft-tissue irritation, a collar (FIGS. 1 and 5: 15 and FIGS. 3 and 6: 13) with a plurality of flutes (17) cut through the periphery and parallel to the longitudinal axis that form elastic prongs (18) to resist collar (FIGS. 1 and 5: 15 and FIGS. 3 and 6: 13) rotation and allow the section of the collar (FIGS. 1 and 5: 15 and FIGS. 3 and 6: 13) body designed to contact cortical bone (21) to act elastically when pressed into or pulled from a cortical bone (21) defect, and a collar (FIGS. 1 and 5: 15 and FIGS. 3 and 6: 13) that is externally grooved or beaded (16) circumferentially to resist forces tending to pull or push out the implant.

The collar (FIGS. 1 and 5: 15 and FIGS. 3 and 6: 13) bore is designed to receive adapters that can act through the bore (12) of the port to facilitate manipulation of bone, marrow and cartilage. Examples of these devices include but are not limited to a biopsy assembly as described for the cancellous access port and bone biopsy implant (U.S. Ser. No. 08/357, 072 and U.S. Pat. No. 5,405,388, previously incorporated herein by reference), electrochemical measuring devices and a tissue containment device as described for the cancellous access port (U.S. Ser. No. 08/357,072, previously incorporated by reference herein); a penetrable seal (19) or an adapter insert (27) with guide tubes (28) for directing surgical instruments such as fiber optics (31), catheters (33) and surgical instruments (32) for manipulation of tissue. Fiber optics (31) may be used for illumination, observation, cauterization, and surgical manipulation. Catheters may be used for infusion or aspiration of body tissue and fluids. Examples of surgical instrument (32) consist of, but are not limited to, a knife, curette, rotating cutter, clipper, or mechanical, chemical, sonic manipulator. The collar (FIGS. 1 and 5: 15 and FIGS. 3 and 6: 13) can, by use of internal fasteners (26) or external fasteners (14), insert devices directly to the collar (13) through the use of threads (29) or through the use of a cap (20). The cap may have a bore (24) to access the penetrable seal (19) and a means such as threads (25) to fasten the cap to the external aspect of the collar (15).

The invention acts to form a port into bone. It maintains an opening through hard cortical bone (21) to allow the manipulation of medullary tissue including cancellous trabecular bone (23), and marrow or bone cells (22), and cortical bone (21) from the inside. Its elastic action of the prongs (18) when press-fit into bone allows it to be placed without the use of special tools to tap the bone defect. The lack of a requirement to place threads into the drill hole eliminates the possibility that the threads will be stripped during taping or insertion of the device. Furthermore the elastic action of the prongs allows the device to be easily removed by pulling the device from the cortical bone (21) defect. The coupled use of a collar (FIGS. 1 and 5: 15 and FIGS. 3 and 6: 13) to maintain an opening and the use of an penetrable seal (19) or adapter insert (27) to fill the bore (12) eliminate any voids that might fill with tissue and block the use of the device. This provides a significant advantage over the prior art.

Further significant advantages over the prior art are achieved through this invention. First the prior art relies on conduits to channel fluids into the bone. Second the prior art can not fabricate their conduits from materials that have an affinity for bone due to the likelihood that these materials will conduct bone into the conduit and chamber and block their use. Third the ability of the subject invention to be fabricated from bone conducting materials such as ceramics or titanium enhance the likelihood of long term fixation of the collar (FIGS. 1 and 5:15 and FIGS. 3 and 6: 13) into the surrounding cortical bone (21) defect. Fourth, an needle (30) for infusion or aspiration when repeatedly pushed through the penetrable seal (19) will cause its failure. The guided needle flapper valve design avoids puncture related mechanical degradation of the diaphragm (FIG. 7). This valve guides a needle (30) through a port (35) and into the striker plate (37) of a flapper valve (36). Fifth, one port can accept a plurality of adapters, inserts and surgical instruments.

The port may have external or internal means of insert fixation. External means of insert fixation is selected from the group consisting of a thread, a structure allowing a press fit, a bead, a groove and an adhesive. Internal means of insert fixation is selected from the group consisting of a thread, a structure allowing a press fit, a bead, a groove and an adhesive.

An adapter insert allows introduction and manipulation of a surgical instrument through the port and into the medullary compartment of bone. In an embodiment of the present invention, the adapter insert may comprise a surgical assembly or surgical instrument selected from the group consisting of a guide tube, fiber optic, catheter, needle, laser scalpel, electrical coagulator, knife, curette, rotating cutter, clipper, flexible shaft cutter, mechanical manipulator, chemical manipulator, and sonic manipulator.

An aspect of the present invention is a method of performing hard tissue surgery selected from the group of surgeries consisting of viewing bone and marrow tissue, cutting medullary tissue, cauterizing medullary tissue, delivering a fluid into the vascular system, delivery of a treatment having solid physical form into bone or medullary tissue, and aspirating a fluid from hard tissue. The method comprises the steps of: preparing a surgical defect in hard tissue to expose medullary tissue, placing the hard tissue implant as described herein into the surgical defect where the surgical assembly or surgical instrument is selected from the group herein described; and performing the hard tissue surgery.

Further advantages will be realized through the use of this invention and embodiment of the subject invention are intended to describe examples and are not intended to limit this invention to just those objects and advantages described.

Figure 1:
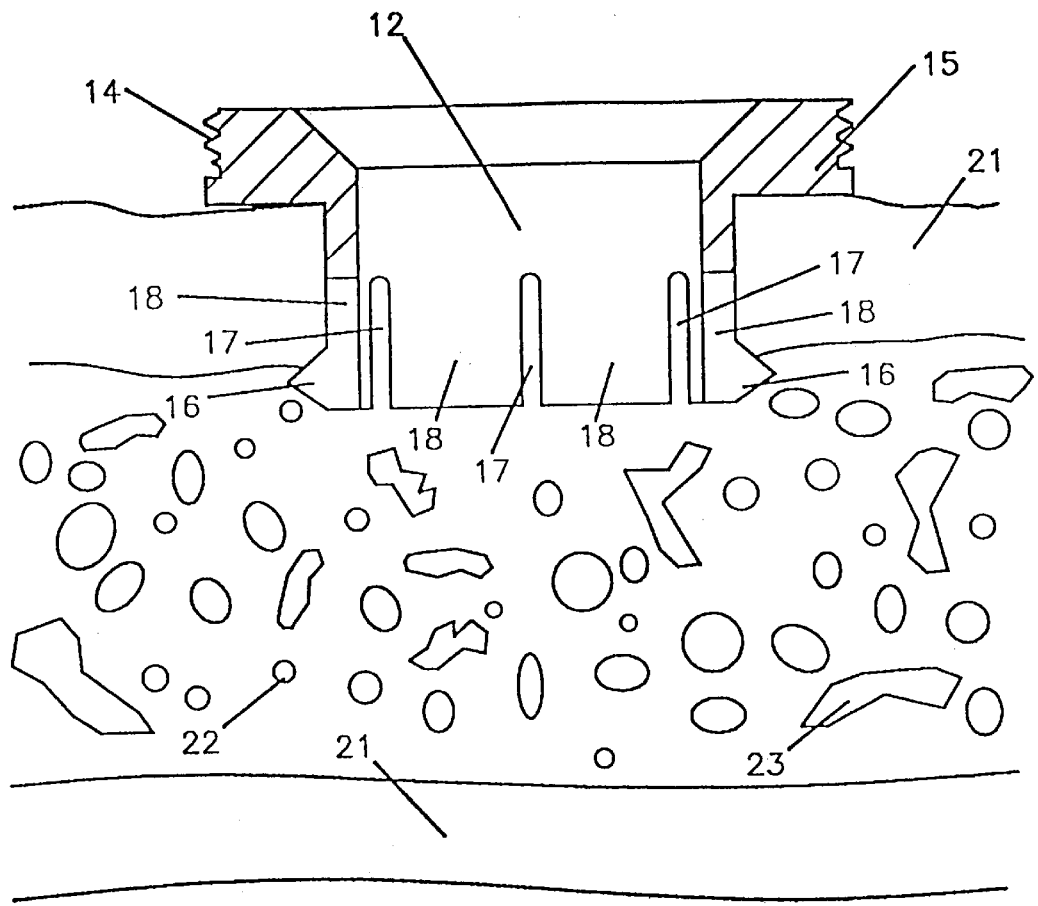
FIG. 1 is a cross-sectional plane view of the implant showing the design of the port with a penetrable seal in situ in bone.
Figure 2:
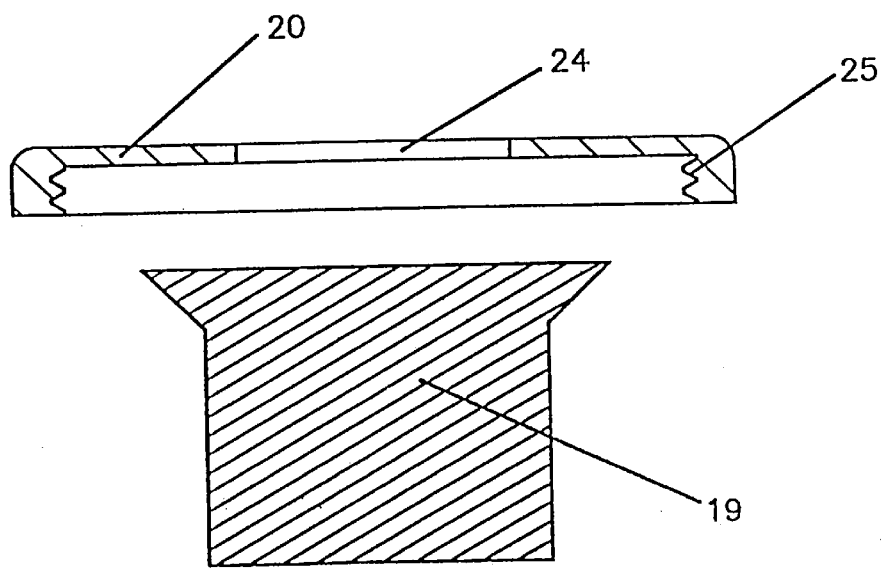
FIG. 2 is a cross-sectional plane view of the penetrable seal and its retaining ring.

LIST OF REFERENCE NUMERALS 12. bore
13. port with internal means of insert fixation
14. port seal ring retaining threads
15. port with external means of insert fixation
16. port anchor bead
17. port flutes
18. elastic prongs
19. penetrable seal bore insert
20. cap
21. cortical bone
22. marrow or bone cells
23. cancellous bone trabeculae
24. seal access bore
25. cap retaining threads
26. port bore adapter insert threads
27. bore adapter insert
28. guide tube
29. bore adapter insert threads
30. infusion or aspiration needle
31. fiber optics for illumination and observation
32. rotating cutter
33. aspiration catheter
34. needle flapper valve
35. needle guide port
36. flapper valve
37. flapper strike plate

DESCRIPTION OF THE PREFERRED EMBODIMENT

Figure 3:
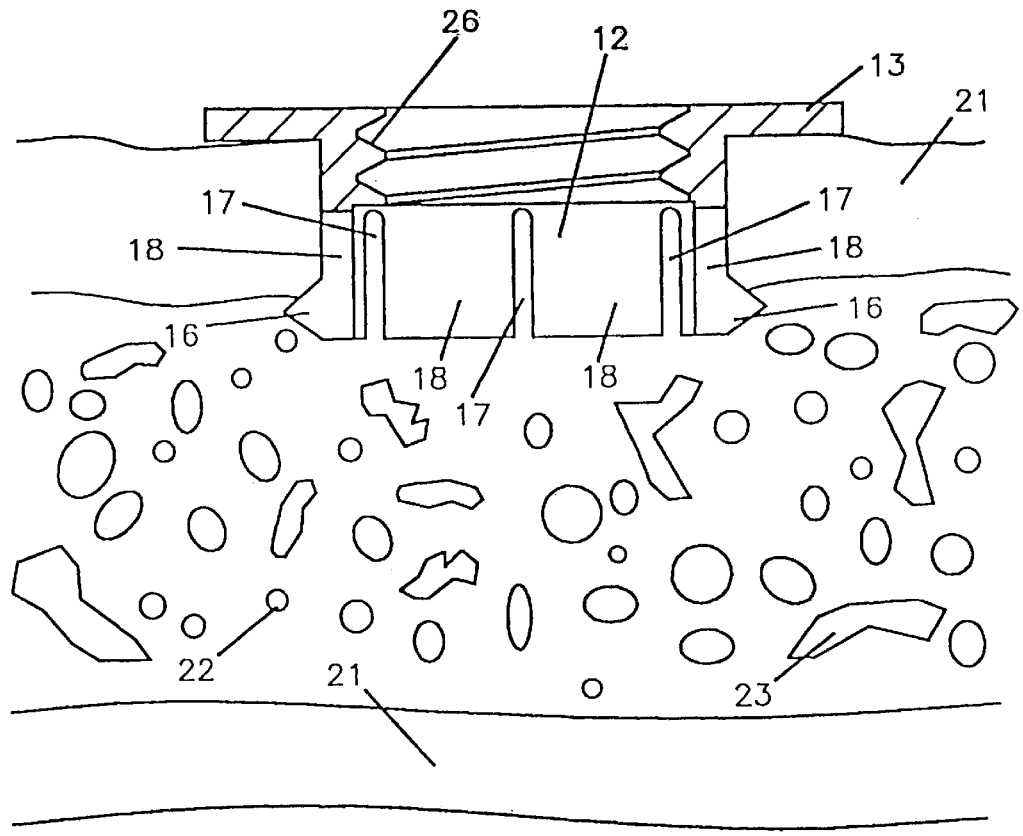
FIG. 3. is a cross-sectional plane view of the implant showing the design of the port for surgical manipulation of bone in situ in bone.
Figure 4:
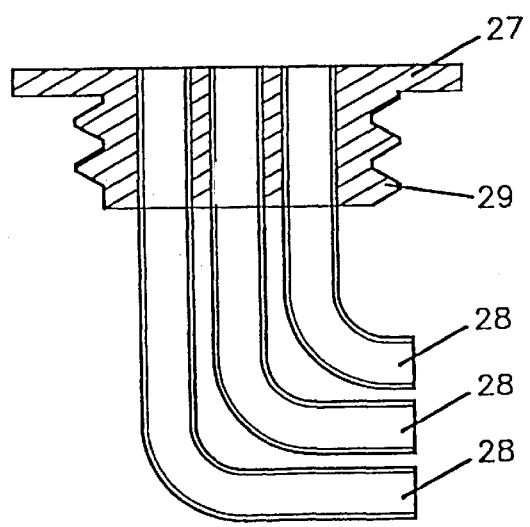
FIG. 4. is a cross-sectional plane view of the adapter insert for the bore of the port with guide tubes for aspiration, viewing and surgery.

The preferred embodiment consists of a single component collar (13) as shown in FIG. 3. The collar (13) is cylindrically shaped with a bead (16) on the outer surface of the collar to engage the surrounding bone (as shown in FIG. 3). The collar (13) has a plurality of flutes (17) cut from the end having the bone locking bead (16) toward the end of the collar (13) having an increased outside diameter. The flutes (17) allow the cylindrical walls of the collar near the end with the bead (16) to act as elastic prongs (18) and strain towards the centrum of the collar (13) when inserting or removing from a bone defect with a size equal to the diameter of the collar (13) but less than the combined diameter of the collar (13) and bead (16). The elastic deforming action of the fluted portion of the collar (13) acts to push the bead (16) into the surrounding bone (21) and cause immediate locking of the collar (13) following insertion. The collar flutes (17) are cut with smooth edges to promote bone ingrowth and collar torsional resistance.

Figure 6:
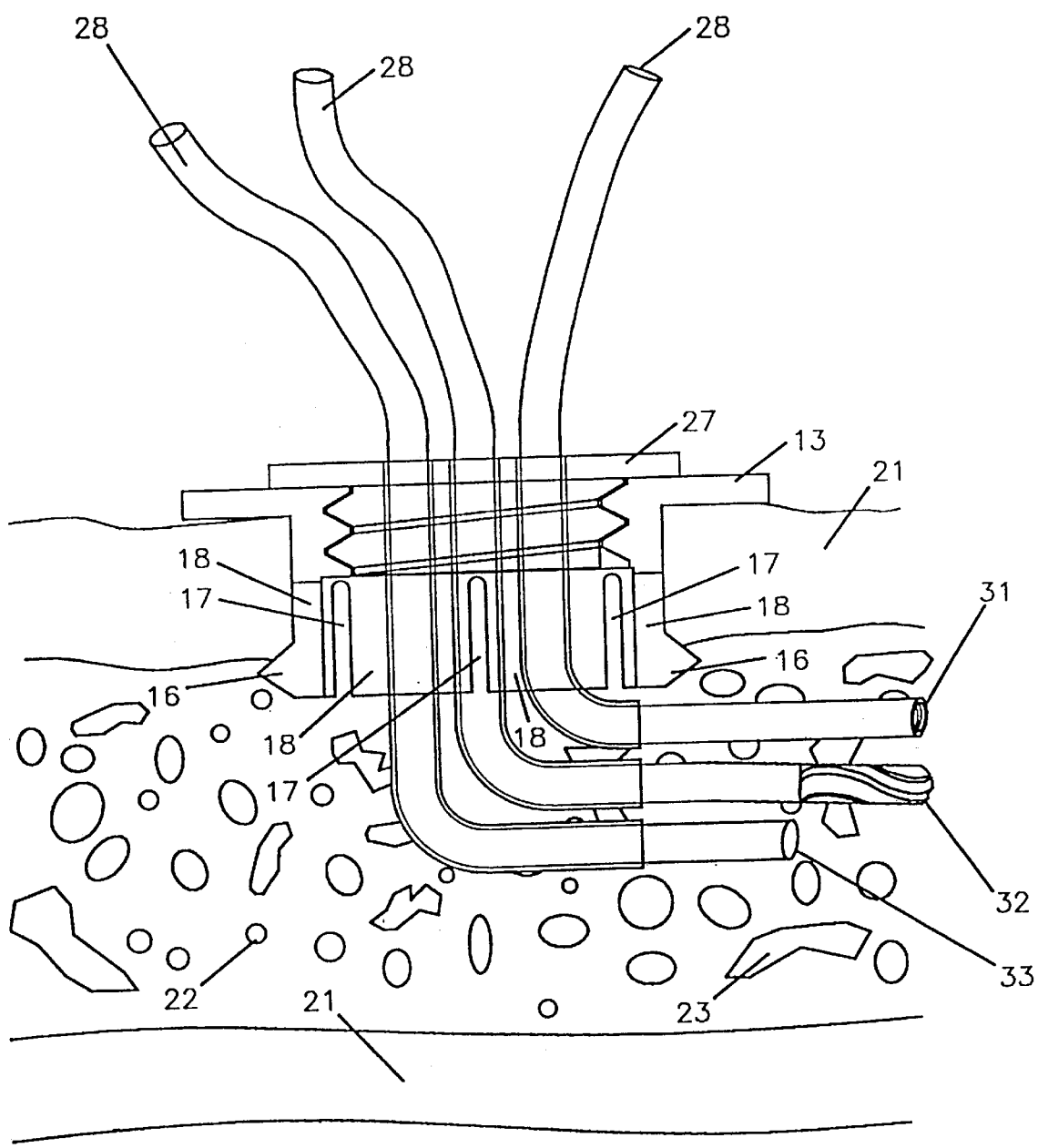
FIG. 6 is a cross-sectional plane view of the port for surgical manipulation of bone with fiber optic for illumination and observation, aspiration tube, and rotary cutter in situ in bone.
Figure 7:
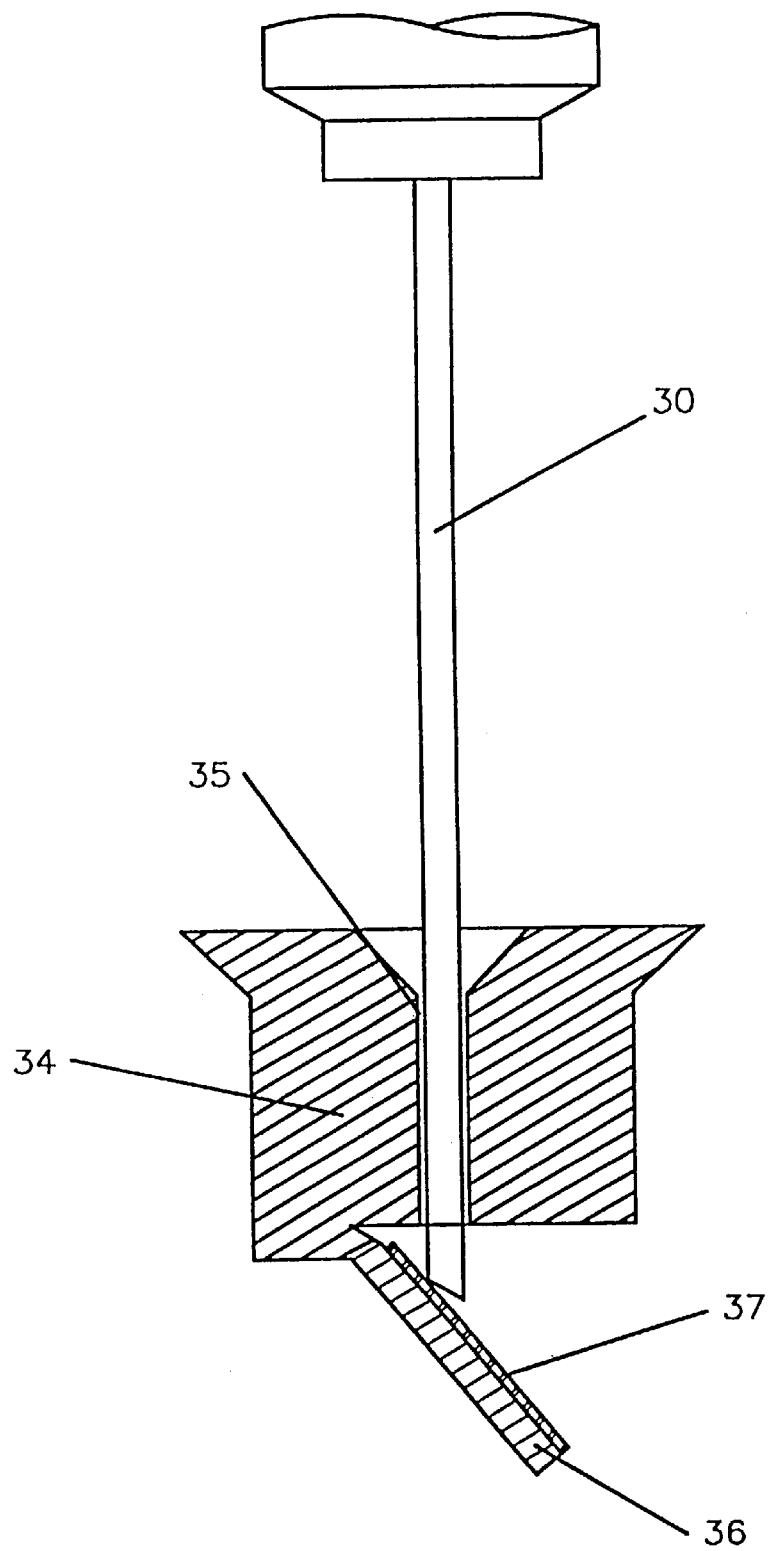
FIG. 7 is a cross-sectional plane view of an infusion port adapter showing sealing mechanism, infusion or aspiration needle and valve mechanism.

As shown in FIG. 3 and FIG. 6, the collar (13) bore (12) is shaped to allow the placement of an adapter insert (27). This adapter (27) impedes extravasation and allows the introduction of needles and instruments through the collar (13) and into the medullary compartment of bone. The adapter attaches to the collar (13) with a bore (12), a seal (19), and a cap (20) with threads (26) cut into the bore (12) to receive an adapter bore insert (27). The insert (27) may have one or a plurality of guide tubes (28) that allow the insertion of needles (30), fiber optics (31), cutters (32) or catheters (33). The guide tube may be biocompatible tubing, a catheter, or a trocar, for example. The guide tubes (28) can be preshaped or formed from shape memory so that when they are subjected to body temperature they return to an original shape that guides the devices down the long axis of the bone.

An alternate embodiment consists of a seal that can lock to the collar (13) by a cap (20) with a bore (24) or other obvious means such as press-fit, grooves in the bore and beads on the seal or biocompatible adhesive. The penetrable seal (19) may be solid or have a small port (35) that runs longitudinally through its central axis and a flapper valve (36). This small bore will open during the insertion of a needle (30) and close when the needle is withdrawn.

OPERATION OF INVENTION

Figure 5:
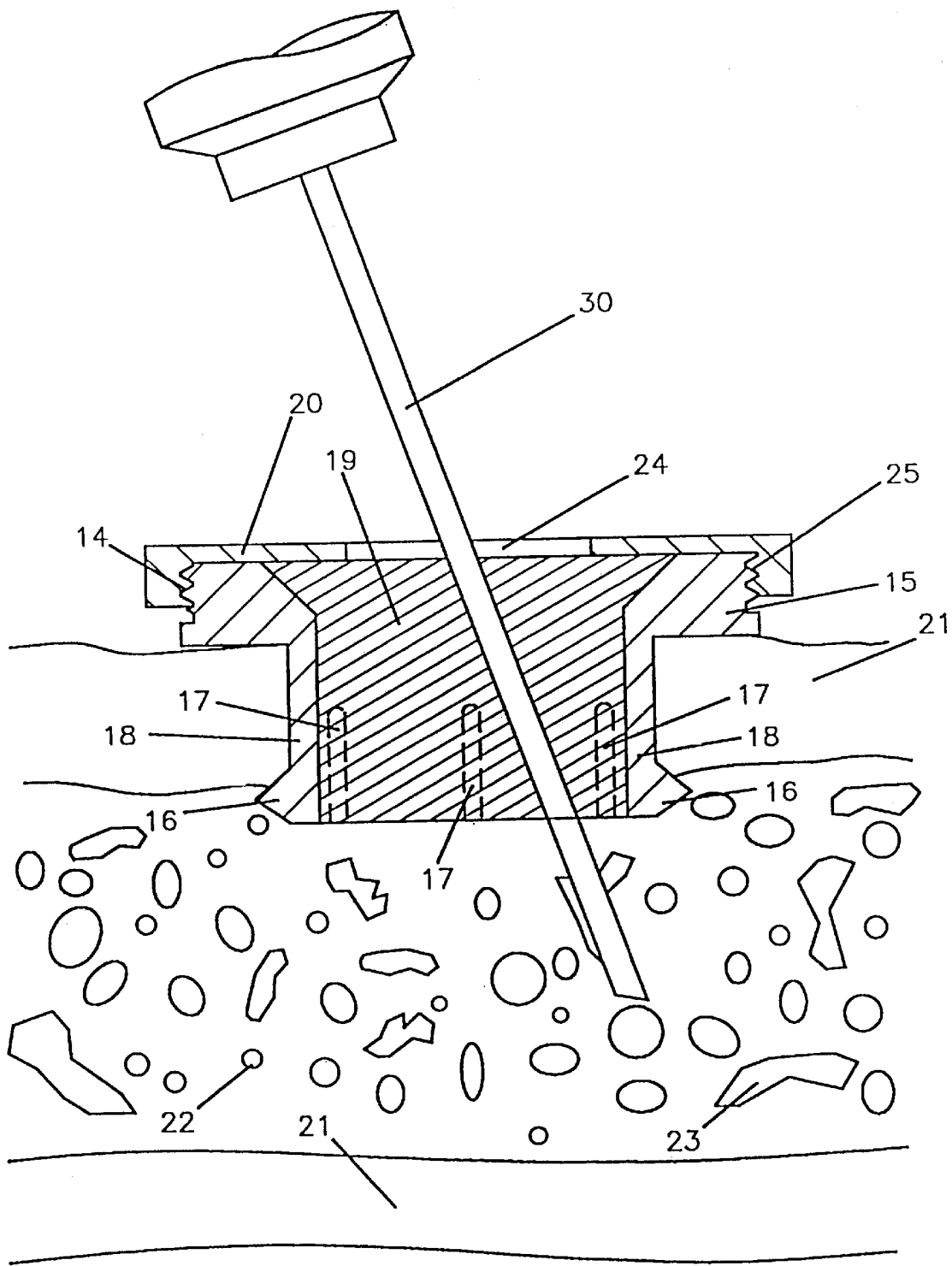
FIG. 5. is a cross-sectional plane view of the port for infusion in situ with ring, seal and port and infusion needle.

The collar (FIGS. 1 and 5: 15 and FIGS. 3 and 6: 13) operates when placed in a circular hole in cortical bone (21) by mechanically locking to the internal surface of the hole. As the collar (FIGS. 1 and 5: 15 and FIGS. 3 and 6: 13) is pushed into the hole, the bead (16) on the outer surface of the fluted end of the implant forces the walls of the fluted end to strain towards the centrum of the collar. This movement of the walls of the collar (FIGS. 1 and 5: 15 and FIGS. 3 and 6: 13) is required because the outside diameter of the collar (FIGS. 1 and 5: 15 and FIGS. 3 and 6: 13) in the area of the bead (16) is greater than the inside diameter of the hole. This elastic strain forces the bead (16) into the internal surface of the hole causing the implant to resist forces which tend to push the collar (FIGS. 1 and 5:15 and FIGS. 3 and 6:13) into bone or pull the collar (FIGS. 1 and 5: 15 and FIGS. 3 and 6: 13) from the hole. In a bone with a thin cortex, the bead (16) may reach through the hole and expand outward causing the bead (16) to partially reach past the backside of the hole, and cause the contour of the bead (16) to direct the elastically generated force in such a way that it pushes against the walls of the cortical bone (21) defect and downward on the collar (FIGS. 1 and 5: 15 and FIGS. 3 and 6: 13) causing the collar (FIGS. 1 and 5: 15 and FIGS. 3 and 6: 13) to further seal against the bone.

Once the collar (FIGS. 1 and 5:15 and FIGS. 3 and 6: 13) is fixed in cortical bone (21), the penetrable seal (19) or insert (27) is placed in the bore (12). If the penetrable seal (19) is used, the skin can be left retracted or sutured closed for subsequent percutaneous access by needle (30).

If the insert (27) is placed to perform bone surgery from the inside of the bone to the outside, instruments are run into the guide tubes to perform surgical manipulation of bone, marrow or cartilage. Non healing fractures of long bone can be treated by implantation of the implant in healthy bone adjacent to the fracture and the manipulation of nonhealing tissue from the inside. This protects the overlying vascular supply, minimizes the potential for infection, reduces morbidity and provides an opportunity to implant a bone scaffolding of osteogenetic substance.

Once the procedure is complete, and if future procedures are anticipated, the instruments are removed and flexible biocompatible wires are inserted in the guide tubes (28) to keep tissue from forming within their inner diameter. The skin is closed over the device. The implant must be surgically accessed to perform future manipulations. If future procedures are not anticipated, the device is pulled from the site and skin is closed over the cortical bone (21) defect.

If the insert (13 or 15) is used as a bone aspirate collection port the aspirate can be collected, separated into vital wound healing components, and administered to the patient. Collection may be vacuum driven. Separation may include centrifugation and filtering. Administration may include the combination of the autologous tissue with donor or synthetic bone replacement material.

I claim:

1. An implant for positioning in hard tissue cortex for surgical instrument access to a medullary compartment of bone or cartilage and for manipulation of bone or marrow, said implant comprising:

a port having
    an outer surface and an inner surface, said inner surface formed by a longitudinally oriented port bore, said port bore having means of insert fixation,
    said port having a predetermined length terminating in a first end and a second end, the first end protruding from hard tissue cortex an amount that allows closure of overlying soft tissue during use, the second end partially reaching beyond the cortex during use,
    a plurality of longitudinally oriented flutes that form prongs, the flutes formed to allow bone ingrowth and to promote port torsional resistance during use, the prongs directing elastically generated force against walls of hard tissue cortex during use,
    the prongs having circumferential beading at the second end of the port, wherein the beading partially reaches beyond the cortex during use thereby exerting a force that pulls the implant toward the medullary compartment of bone during use; and
  an insert for insertion into said port bore and for use with a surgical instrument, said insert having
    means of insert fixation complementary to said means for fixation into the port bore,
    a length and a diameter to substantially fill the port bore thereby preventing blockage of the port during use,
    said insert selected from the group consisting of
      i. a penetrable, non-osseous-integrating plug,
      ii. a combination of
        a. an adapter having a bore for insertion of a surgical instrument, and
        b. a surgical instrument fittable into the adapter bore selected from the group consisting of a knife, curette, rotating cutter, flexible shaft cutter, clipper, laser scalpel, electrical coagulator, mechanical manipulator, chemical manipulator, and sonic manipulator,
      iii. an adapter having a bore, the bore fitted with a penetrable, non-osseous-integrating plug, iv. a combination of
   a. a penetrable, non-osseous-integrating plug, and
   b. a surgically-related instrument, the instrument positioned within the penetrable plug, and
v. a combination of
   a. an adapter having a bore, the bore fitted with a penetrable, non-osseous-integrating plug, and
   b. a surgically-related instrument, the instrument positioned within the penetrable plug.

2. The implant according to claim 1, wherein said insert is insert ii) or iii) formed from a biocompatible material selected from the group consisting of titanium, stainless steel, a chromium cobalt alloy, silica glass, calcium phosphates, calcium carbonate, a silicone elastomer and polyethylene.

3. The implant of claim 1 wherein said insert is insert i).

4. The implant of claim 1 wherein said insert is insert ii) and the insert is further in combination with a guide tube, the guide tube positioned within the bore of the adapter for insertion of the surgical instrument.

5. The implant of claim 1 wherein said first end protruding from hard tissue cortex has external means of insert fixation.

6. The implant of claim 1 wherein said port bore means of insert fixation is internal and is selected from the group consisting of a thread, a structure allowing a press fit, a bead, a groove and an adhesive.

7. The implant of claim 5 wherein said external means of insert fixation is selected from the group consisting of a thread, a structure allowing a press fit, a bead, a groove and an adhesive.

8. The implant of claim 3 wherein said non-osseous-integrating plug is a polyethylene or teflon plug.

9. The implant of claim 3 wherein said non-osseous-integrating plug is a silicone elastomer plug.

10. The implant of claim 1 wherein said insert is insert iv).

11. The implant of claim 10 wherein said surgically-related instrument is selected from the group consisting of a needle, a catheter, a fiber optic, a laser scalpel, an electric coagulator, and a flexible shaft cutter.

12. The implant of claim 1 wherein said insert is insert ii) and the insert is a bone biopsy assembly for manipulation of bone, marrow or cartilage.

13. The implant of claim 1 wherein said insert is insert ii) and the insert is an electrochemical measuring device.

14. The implant of claim 1 wherein said insert is insert ii) and the insert is a tissue containment device.

15. The implant of claim 4 wherein the guide tube is selected from the group consisting of a catheter and a trocar.

16. The implant of claim 10 wherein said surgically-related instrument is selected from the group consisting of a needle, fiber optic and a catheter.

17. The implant of claim 3 further comprising a cap for locking to the port.

18. The implant of claim 17 wherein said cap has an insert access bore.

19. The implant of claim 3 wherein said penetrable non-osseous-integrating plug comprises a guide port and a flapper valve, wherein the guide port extends through the penetrable plug to the flapper valve and the flapper valve opens to expose medullary tissue when in use.

20. The implant of claim 19 wherein the flapper valve has a guide port side and a medullary compartment side, and wherein the penetrable plug further comprises a flapper strike plate positioned on the guide port side of the flapper valve.

21. A method of performing surgery of hard tissue or hard tissue marrow comprising positioning said implant of claim 1 into hard tissue; and performing surgery of hard tissue or hard tissue marrow.

22. The method of claim 21 wherein the step of performing surgery is from within bone.

23. The implant of claim 1 wherein said insert is insert iii.

24. An implant for positioning in hard tissue cortex for surgical instrument access to a medullary compartment of bone or cartilage and for manipulation of bone or marrow, said implant comprising:

a port having
   an outer surface and an inner surface, said inner surface formed by a longitudinally oriented port bore, said port bore having means of insert fixation,
   a predetermined length terminating in a first end and a second end, the first end protruding from hard tissue cortex an amount that allows closure of overlying soft tissue during use, the second end partially reaching beyond the cortex during use,
   a plurality of longitudinally oriented flutes that form prongs, the flutes formed to allow bone ingrowth and to promote port torsional resistance during use, the prongs directing elastically generated force against walls of hard tissue cortex during use,
   the prongs having circumferential beading at the second end of the port, wherein the beading partially reaches beyond the cortex during use thereby exerting a force that pulls the implant toward the medullary compartment of bone during use; and
an insert for insertion into said port bore and for use with a surgical instrument, said insert having
   means of insert fixation complementary to said means for fixation into the port bore,
   a length and a diameter to substantially fill the port bore thereby preventing blockage of the port during use,
   wherein said insert is a combination of
      a. an adapter having an adapter bore,
      b. a guide tube fitted into the adapter bore, and
      c. a biocompatible wire fitted into the guide tube for preventing tissue formation within the guide tube.

* * * * *

UNITED STATES PATENT AND TRADEMARK OFFICE
CERTIFICATE OF CORRECTION

PATENT NO. : 5,990,382
DATED : November 23, 1999
INVENTOR(S) : William Casey Fox It is certified that error appears in the above-identified patent and that said Letters Patent is hereby corrected as shown below:

In Claim 1, column 9, line 2, delete the period "." After the word 'penetrable', and insert a comma --,--, therefor.

In Claim 2, column 9, line 14, delete the word "phosphates" and insert --phosphate--, therefor.

Signed and Sealed this

Thirtieth Day of May, 2000

*Attest:*

Q. TODD DICKINSON

*Attesting Officer*   *Director of Patents and Trademarks*